United States Patent
Edvinsson et al.

(10) Patent No.: US 8,273,771 B2
(45) Date of Patent: Sep. 25, 2012

(54) ISCHEMIC DISORDER OR DISEASE INHIBITORS

(75) Inventors: Lars Edvinsson, Lund (SE); Saema Ansar, Staffanstorp (SE)

(73) Assignee: Pronas Pharma AB, Malmo (SE)

( * ) Notice: Subject to any disclaimer, the term of this patent is extended or adjusted under 35 U.S.C. 154(b) by 310 days.

(21) Appl. No.: 12/594,130

(22) PCT Filed: Mar. 25, 2008

(86) PCT No.: PCT/SE2008/000218
§ 371 (c)(1),
(2), (4) Date: Mar. 1, 2010

(87) PCT Pub. No.: WO2008/121044
PCT Pub. Date: Oct. 9, 2008

(65) Prior Publication Data
US 2010/0152248 A1    Jun. 17, 2010

(30) Foreign Application Priority Data

Mar. 30, 2007 (SE) ...................................... 0700814

(51) Int. Cl.
*A61K 31/4439* (2006.01)
*A61K 31/277* (2006.01)
(52) U.S. Cl. ........................................ 514/341; 514/523
(58) Field of Classification Search .................. 514/341, 514/523
See application file for complete search history.

(56) References Cited

U.S. PATENT DOCUMENTS
2010/0152248 A1* 6/2010 Edvinsson et al. ............ 514/341

FOREIGN PATENT DOCUMENTS
WO    WO 02/28388 A2    4/2002
WO    WO 2006/130090 A1    12/2006

OTHER PUBLICATIONS

Extended European Search Report for corresponding European Patent Application No. 08724144.4 mailed May 6, 2010.
Ansar, S. et al. "Subtype Activation and Interaction of Protein Kinase C and Mitogen-Activated Protein Kinase Controlling Receptor Expression in Cerebral Arteries and Microvessels After Subarachnoid Hemorrhage", *Stroke*, 2008, pp. 185-190.
Sakurada, O. et al. "Local cerebral glucose utilization following injection of β-endorphin into periaqueductal gray matter in the rat", *Brain Research*, vol. 153, 1978, pp. 403-407.
Bederson, J. et al. "Rat middle cerebral artery occlusion: evaluation of the model and development of a neurologic examination", *Stroke*, vol. 17, 1986, pp. 472-476.
Mulvany, M. et al. "Contractile properties of small arterial resistance vessels in spontaneously hypersensitive and normotensive rats", *Circulation Research*, vol. 41, 1977, pp. 19-26.
O'Collins, V. et al. 1,026 Experimental Treatments in Acute Stroke, *American Neurological Association*, 2006, pp. 467-477.
Takle, A. et al. "The Identification of Potent and Selective Imidazole-based Inhibitors of B-Raf Kinase", *Bioorganic & Medicinal Chemistry Letters*, vol. 16, 2006, pp. 378-381.
Namura, S. et al. "Intravenous administration of MEK inhibitor U0126 affords brain protection against forebrain ischemia and focal cerebral ischemia", *PNAS*, vol. 98, No. 20, 2001, pp. 11569-11574.
Jamali, R. et al. "Involvement of Protein Kinases on the Upregulation of Endothelin Receptors in Rat Basilar and Mesenteric Arteries", *Exp. Biol. Med.*, vol. 231, 2006, pp. 403-411.
Beg, S. et al. "Protein kinase C inhibition prevents upregulation of vascular ET B and 5-HT 1B receptors and reverses cerebral blood flow reductions after subarachnoid hemorrhage in rats", *Journal of Cerebral Blood Flow & Metabolism*, vol. 27, No. 1, 2007, pp. 21-32.
Beg, S. et al. "ERK1/2 inhibition attenuates cerebral blood flow reduction and abolishes ET B and 5-HT 1B receptor upregulation after subarachnoid hemorrhage in rat".
Wieloch, T. "Molecular Mechanisma of Ischemic Brain Damage", Cerebral Blood Flow and Metabolism, $2^{nd}$ Edition, pp. 423-451.
"Abstracts from the $12^{th}$ Annual Meeting of the European Council for Cardiovascular Research (EECR)", *Hypertension*, vol. 50, No. 4, Oct. 207, pp. 799-823.
Henriksoon, M. et al. "MEK1/2 inhibition attenuates vascular ETA and ETB receptor alterations after cerebral ischaemia", *Experimental Brain Research*, vol. 178, No. 4, Nov. 8, 2006, pp. 470-476.
King, A. et al. "Demonstration of a genetic therapeutic index for tumors expressing oncogenic BRAF by the kinase inhibitor SB-590885", *Cancer Research*, vol. 66, No. 23, Dec. 2006, pp. 11100-11105.

* cited by examiner

*Primary Examiner* — Raymond Henley, III
(74) *Attorney, Agent, or Firm* — Merchant & Gould P.C.

(57) ABSTRACT

The invention relates to the use of at least on inhibitor selected from the group consisting of raf-, protein kinase C (PKC)-, MEK1/2-, or ERK1/2-inhibitors, for the manufacturing of a medicament to be administrated from 1 up to 12 hours after initiation of an ischemic disease.

11 Claims, 1 Drawing Sheet

ISCHEMIC DISORDER OR DISEASE INHIBITORS

Figure 1A:
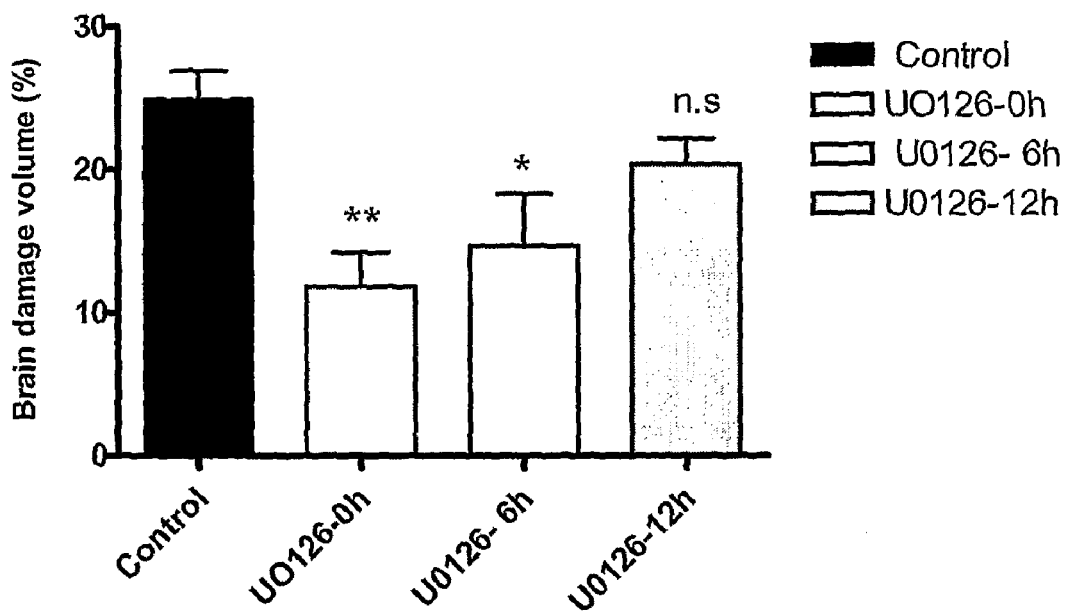

This application is a National Stage Application of PCT/SE2008/000218, filed 25 Mar. 2008, which claims benefit of Serial No. 0700814-7, filed 30 Mar. 2007 in Sweden and which application(s) are incorporated herein by reference. To the extent appropriate, a claim of priority is made to each of the above disclosed applications.

FIELD OF INVENTION

The invention relates to the use of at least one inhibitor selected from the group consisting of raf, protein kinase C (PKC), MEK1/2, or ERK1/2, for the manufacturing of a medicament to be administrated from 1 up to 12 hours after initiation of an ischemic disease.

BACKGROUND OF INVENTION

Stroke is the third leading cause of death in many industrial countries. Around 20% of the patients do not survive the first month and >30% who are alive 6 months later will be dependent on other people. Stroke is often ischemic and the majority of ischemic strokes are the result of an occlusion of a major cerebral artery by a thrombus or an embolism, which give rise to loss of blood flow in one or more specific regions.

Today there are two alternative ways for the treatment of stroke. One way is to try to establish reperfusion to the compromised region by dissolution of the clot using thrombolytic agents. Today, the recombinant tissue-plasminogen activator (rt-PA) is the only thrombolytic agent approved to be used for the treatment of acute ischemic brain injury. The use of rt-PA is restricted to administration within 3 hours after the stroke has occurred. However, its use increases the risk of haemorrhagic transformation, which limits its use. The second way is to develop compounds, which interfere with the biochemical pathway that leads to cell death. By such an approach the core area of injury will not be saved. However, the surrounding area called the ischemic penumbral area (or simply the penumbra) might be saved and the degree of damage restricted.

So far all the agents developed, which were supposed to save the penumbral area, failed to convincingly show efficacy in clinical trials despite they had shown good potential results in animal models. Examples of such compounds are NMDA receptor antagonists, Kappa opioid peptide receptor antagonists, NO inhibitors, $Na^+$ channel blockers, $K^+$ channel blockers, and cell membrane stabilisers, among others (O'Collons V E et al., 2006, 1026 experimental treatments in acute stroke. Ann. Neurol. 59; 467-477).

Other treatments are mainly focused on preventive pharmacotherapy, e.g., by use of antihypertensive agents, antilipids or anticoagulants. Current treatment also relates to alternate ways of cooling the patients, in order to mitigate the negative effect of a stroke. Therefore, recorded treatments are insufficient, or, they can be considered as supportive and synergistic to future regimens emanating from the present invention.

The past 20 years have focused on the mechanisms of ischemic brain damage within the brain tissue per se; the work is related to free radical-mediated damage (Chan P H, Reactive oxygen radical signalling and damage in the ischemic brain. J Cereb Blood Flow Metab 2001; 21:2-14), apoptosis (MacManus J P, Buchan A M. Apoptosis after experimental stroke: fact or fashion? J Neurotrauma 2000; 17:899-914), gene expression (Sharp F R et al. Multiple molecular penumbras after focal cerebral ischemia. J Cereb Blood Flow Metab 2000; 20:1011-1032), and inflammation (Iadecola C, Alexander M. Cerebral ischemia and inflammation. Curr Opin Neurol 2001; 14:89-94) all within the brain tissue/neurons (Wieloch T. Molecular mechanisms of ischemic brain damage. In Cerebral Blood Flow and Metabolism, ed by L Edvinsson and D N Krause, Lippincott Williams Wilkins, Philadelphia 2002, pp 423-451). In particular there has been a focus on NMDA receptors and calcium toxicity as a primary trigger in ischemia. This has been a target in pharmacology to search for the molecular mechanisms of ischemic brain damage and for neuroprotective compounds against ischemic injury. To date, however, no successful clinical stroke trial has appeared (Lees K R. Neuroprotection. Br Med Bull 2000; 56:401-412, O'Collons V E et al., 2006, 1026 experimental treatments in acute stroke. Ann. Neurol. 59; 467-477). In all the work during the past 20 years the main focus has been directed towards the molecular mechanisms within the brain neurons. A hypothetical vascular involvement is regarded as a passive secondary event that by and large has been left out from the discussions, probably because vasodilator drugs are inactive.

Acute focal cerebral ischemia (stroke) results in a severely ischemic core with low residual cerebral blood flow (CBF) whereas the ischemic penumbra synaptic activity is reduced while the residual CBF is enough to maintain membrane ionic gradients. In principle, nerve cells in the penumbral zone can be salvaged after a cerebral ischemic episode; most neurologists have witnessed this fact in the form of patients' recovery of normal motor function within 24 hours after acute hemiparesis. Such cases indicate the complex and variable nature of blood flow reduction in stroke as well as the potential to reverse events related to the penumbral zone after acute cerebral infarction. The expansion of depolarized core coincides with the occurrence of spontaneous peri-infarct spreading depolarization. The tissue viability threshold and its relationship to the penumbra has focused on electrical and membrane failure in brain tissue, and therefore, it has been suggested that the ischemic depolarization increases the metabolic burden, thereby exacerbates the energy deficit, and enlarges the infarct. This view has by and large neglected the fact that stroke primarily is a cerebrovascular disorder. Recently, data was presented that there is neurovascular vasoconstrictor coupling during the ischemic depolarization which contributes to the hemodynamic progression of damage in focal cerebral ischemia.

We have observed a rapid transcriptional upregulation of contractile endothelin-1, and angiotensin II receptors in vascular smooth muscle cells in the middle cerebral artery (MCA) leading to the ischemic region starting immediately after induction of the cerebral ischemia. These changes result in enhanced contraction of the vasculature leading to the ischemic region, particularly because agonists for these receptor are produced in the cerebrovascular endothelium. In agreement, single receptor inhibition has in the past only been found to have limited effect in reducing cerebral infarct size after focal ischemia. Therefore, we hypothesize that blocking the transcriptional upregulation of PKCα and PKCβ that are the key subtypes of PKC, or raf→MEK1/2→ERK1/2 that are involved in the MAPK pathways. We have in experimental work on first isolated brain vessels and then in vivo found that interaction with these protein kinases blocks the upregulation of vascular receptors specifically in association with the ischemic region. We have furthermore found that the two pathways PKC and MAPK ERK1/2 may interact (Ansar & Edvinsson, Stroke 2008). By specific blockade of either or both will reduce the cerebral infarct that occurs after focal cerebral ischemia and normalize the neurology deficit.

Consequently, there is a need for new agents to be used for the treatment of stroke as well as screening methods to enable the finding of new bioactive agents that can be used to efficiently treat ischemic brain injury, to save the penumbral area and help the patient to get a better quality of life. Today, such agents are not available, agents, which are safe, non-addictive and effective, and also to which the body in the long-term is not refractory.

SUMMARY OF THE INVENTION

The invention relates to the use of at least one inhibitors selected from the group consisting of subtype of protein kinase C (PKC), raf, MEK1/2, or ERK1/2, for the manufacturing of a medicament to be administrated from >1 up to 12 hours after the initiation of an ischemic disease. The inventors have surprisingly found that specific subtypes of the MAPK and PKC pathways are activated in cerebral arteries after subarachnoid hemorrhage (SAH) and cerebral ischemia, the PKC and MAPK inhibitors are able to prevent this activation, i.e., both inhibitors against the MAPK as well as the PKC pathways can be utilised to treat an ischemic disease. Additionally, it has surprisingly been found that administration of the inhibitor up to 12 hours after SAH an effect is observed and a reduction in ischemic damage as well as a reduction of the infarct size, regional cerebral blood flow and neurology deficit, and receptor expression in the ischemic region.

A new and invented medicament is obtained, wherein it for the first time is possible to treat a patient suffering from ischemic damage after several hours, which improves the possibilities for the patient to recover from ischemic damage back to the same life as prior to the ischemic damage. Often the patient does not enter a medical care unit until a subset of hours has lapsed and earlier there has been no way to cure the patient when the patient arrives to the hospital. By the new invented invention it will be possible to treat a patient that enters the hospital after several hours after the initiation of ischemic damage. The invention will increase the life of the patient as well as reduce the costs for the medical care. It will be possible to treat the patient much earlier and perhaps already in the emergency situation since the preliminary data show that the medication is not affecting the circulation in any way when administered.

By the use of the medicament and the possibility to treat the patient after several hours after the ischemic damage has occurred the blood flow to the penumbra will be restored, and consequently reduce neural damage in the stroke area. By such a treatment there is an increased possibility that patients suffering from ischemic brain injury will recover and, subsequently, have better chances of a normal life, as compared to the treatments that are available today.

The invention is also related to an in vitro method to screen for the inhibitors useful to treat a patient suffering from ischemic damage comprising the steps of: We have found that by removing a small cerebral artery from a patient or an animal and putting it in an organ culture situation this will result in a receptor upregulation that resembles that seen in stroke. This method is novel and can be used to screen for agents that will modify the receptor changes and allow delineation of substances that can be tested in vivo in patients.

DETAILED DESCRIPTION OF THE INVENTION

In the context of the present application and invention the following definitions apply:

The term "treatment" according to this invention means that by inhibiting the signal resulting in transcription and translation, the receptor upregulation will be prevented and, hence, the sequels leading to penumbral zone damage and neuronal loss will be revoked.

The term "Pharmaceutically acceptable" means a non-toxic material that does not decrease the effectiveness of the biological activity of the active ingredients, i.e., the antimicrobial peptide(s). Such pharmaceutically acceptable buffers, carriers or excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000).

Medicament

The invention relates to the development of a medicament which can be used up to several hours after the onset of an ischemic damage in a patient. This is the first time it has been shown that it is possible to treat a patient suffering from ischemic damage after several hours. The invention relates to the use of at least one inhibitors selected from the group consisting of protein kinase C (PKC), raf, MEK1/2, or ERK1/2, for the manufacturing of a medicament to be administrated from >1 up to 12 from diagnosis of an ischemic disease. The medicament can be administrated up to 12 hours after onset of ischemic damage and still there is an effect. The administration may occur after 1, 2, 3, 4, 5, 6, 7, 8, 9, 10, 11 or 12 hours after the onset of ischemic damage. The inhibitor may be different but the same results have been found using different inhibitors (see examples). The inhibitor may be a PKC inhibitor such as RO-32-0432 or RO-31-7549 which may be obtained from www.calbiochem, cat no: 557508 and 557525. RO-32-0432 is a selective cell-permeable protein kinase C inhibitor active against PKC α and PKC β. RO31-7549 is a selective protein kinase C inhibitor that acts at the ATP binding site of PKC. Other potential inhibitors are U 0126 which is a potent inhibitor of MEK1 and MEK2. U0126 can be purchased from www.calbiochem.com, cat no. 662005. Other inhibitors are th raf inhibitors SB 386023-b and SB590885 which can be obtained from GSK, UK. SB590885 was published in Takle et al., 2006 in Bioorganic & Medical Chemistry Letter, 378-381.

The medicament can be administrated to a patient suffering from ischemic damage starting from 1 hour up to 12 hours, such as from 4 to 10 hours. Specific examples are 2, 3, 4, 5, 6, 7, 8, 9, 10, 11 or 12 hours after onset of ischemic damage and still be able to reduce the damage.

The pharmaceutical medicament will be administrated to a patient in a pharmaceutically effective dose. By "pharmaceutically effective dose" is meant a dose that is sufficient to produce the desired effects in relation to the condition for which it is administered, such as those. The exact dose is dependent on the, activity of the compound, manner of administration, nature and severity of the disorder, age and body weight of the patient different doses may be needed. The administration of the dose can be carried out both by single administration in the form of an individual dose unit or else several smaller dose units and also by multiple administration of subdivided doses at specific intervals. Previous studies on the drugs have used doses much lower and never studied the vascular receptor upregulation in relation to therapeutic responses.

Examples of doses of the active component in the medicament may be from >1 microgram to 100 mg/kg, depending on which inhibitor that will be used as well as the way of administrating said medicament. For example U0126 may be administrated in an amount from 10 to 50 mg/kg. For example SB386023-b or RO-31-7549 may be administered in an amount of 1 microgram to 10 mg/kg. For systemic administration the dose is calculated per 70-80 kg body weight; for intraventricular administration it is calculated on the basis of brain weight (1.5 kg) and hence the mg dosage is much less. Systemic administration to a patient having a weight of 70 kg wherein a single dose should be 10 mg/kg would be a dose of 700 mg. Treatment of the same patient intraventricular would be 1.5 kg×10=15 mg" The medicament may further comprises a pharmaceutically acceptable diluent, excipient, buffer or carrier.

The term "buffer" is intended to mean an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

The term "diluent" is intended to mean an aqueous or non-aqueous solution with the purpose of diluting the active ingredient in the pharmaceutical preparation. The diluent may be one or more of saline, water, polyethylene glycol, propylene glycol, ethanol, DMSO or oils (such as safflower oil, corn oil, peanut oil, cottonseed oil or sesame oil).

The excipient may be added to enhance or maintain the solubility of the active ingredient (solubilizers) and/or stability (buffer, antioxidants and chelating agents). Exipients can also be used as preservatives and tonicity agents. Examples may be one or more of carbohydrates, polymers, lipids and minerals. Examples of carbohydrates include lactose, sucrose, mannitol, and cyclodextrines, which are added to the composition, e.g., for facilitating lyophilisation. Examples of polymers are starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone, all of different molecular weight, which are added to the composition, e.g., for viscosity control, for achieving bioadhesion, or for protecting the active ingredient from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers.

The medicament may be administrated intravenously or intrathecally or intravectricullarly. One specific example being that the medicament is administrated intravectricullarly. For subarachnoid haemorrhage it will be given into the cerebrospinal fluid of patients to have no systemic side effects. When it is given for cerebral ischemia (e.g. thromboembolic) it will be given intravenously. Both routes will be used for treatment in a period of 1 to 2 weeks. Our present data have shown that the drugs exemplified have no systemic side effects in the doses given above.

Screening Method

The invention also relates to a new method in which human arteries for the first time are utilised to identify inhibitors selected from the group consisting of protein kinase C (PKC), raf, MEK1/2, or ERK1/2. By the use of arteries isolated from human beings a number of problems are solved compared to when other non-human materials are used. To be able to identify such inhibitors there is a need for one or more model system in which vasoconstriction and/or vasodilation may be induced in parallel or in sequence with upregulation of one or more receptors, such as endothelin, angiotensin, serotonin and/or bradykinin. The inventors have surprisingly found that blood vessels from human beings subjected to ischemia undergoes phenotypic changes so that the vasoconstrictor receptor population is upregulated, which result in arterial constriction, and that for example the endothelin and the 5-carboxamidotryptamine receptors are among those becoming upregulated.

By the use of human arteries it is for the first time possible to identify inhibitors that surely are active against human tissue and which by a high probability effectively can be used to treat a human being suffering from ischemia. Additionally it is also possible in a fast and efficient way notice if the invented agents are toxic to human cells or not, which can be different between cells having different origins. The new invented method will increase the speed to identify inhibitors that further could be developed into functional pharmaceutical compositions.

The arteries are exposed to physiological solution, in which the receptors can be upregulated. Example of such a solution is DMEM, well known for a person skilled in the art.

The arteries may be dissected into smaller segments or discs either prior to or after upregulation of one or more receptors.

The arteries may be obtained from a patient suffering from ischemia. The isolated arteries will then be immersed in a solution to maintain their biological activities, also exposed to a tension, in order to enable the possibility to study vasoconstriction and/or vasodilation. One way to study isomeric tension is to use a Mulvany-Halpern Myogrph (Danish Myo Technology A/S, Denmark). The arteries are then exposed to an agent which might be an inhibitor and the contractile response is studied. If the response is reduced the agent is determined as being a candidate for further evaluation as a pharmaceutical agent against ischemia.

Finally, the invention relates to a method of treating a mammal in need thereof by the use of a medicament according to any of preceding claims.

Following examples are intended to illustrate, but not to limit, the invention in any manner, shape, or form, either explicitly or implicitly.

EXAMPLES

Example 1

All animal procedures were carried out strictly within national laws and guidelines and approved by the Danish Animal Experimentation Inspectorate and the Ethical Committee for Laboratory Animal Experiments at the University of Lund.

Example 2

Rat Subarachnoid Hemorrhage Model

Subarachnoid hemorrhage was induced by a model originally devised by Svendgaard et al and carefully described by Prunell et al (2003). Male Sprague-Dawley rats (350-400 g) were anaesthetized using 5% halothane (Halocarbon Laboratories, River Edge, N.J.) in $N_2O/O_2$ (30:70). The rat was intubated and artificially ventilated with inhalation of 0.5-1.5% halothane in $N_2O/O_2$ (70:30) during the surgical procedure. The depth of anaesthesia was carefully monitored and the respiration checked by regularly withdrawing arterial blood samples for blood gas analysis (Radiometer, Copenhagen, Denmark). An electric temperature probe was inserted into the rectum of the rat to record the temperature, which was maintained at 37° C. An arterial catheter to measure blood pressure was placed in the tail artery and a catheter to monitor intracranial pressure (ICP) was placed in the subarachnoid space under the subocciptal membrane. At either side of the skull, 3 mm from the midline and 4 mm anteriorly from the bregma, holes were drilled through the skull bone down to dura mater (without perforation) allowing the placement of two laser-Doppler flow probes to measure cortical CBF. Finally, a 27G blunt canula with side hole was introduced 6.5 mm anterior to bregma in the midline at an angle of 30° to the vertical. With the aperture pointing to the right, the needle was lowered until the tip reached the skull base 2 to 33 mm anterior to the chiasma. After 30 minutes of equilibration 250 µl blood was withdrawn from the tail catheter and injected intracranially via this canula at a pressure equal to the mean arterial blood pressure (MABP) (80-100 mmHg). Subsequently the rat was kept under anaesthesia for another 60 minutes to allow recovery from the cerebral insult after which catheters were removed and incisions closed. The rat was then revitalized and extubated. A subcutaneous injection of carprofen (4.0 mg/kg) (Pfizer, Denmark) was administered and the rat was hydrated subcutaneously using 40 ml isotonic sodium chloride at the end of the operation and at day one.

During the period, the rat was monitored regularly, and if showing severe distress the animal was prematurely killed. In addition, a series of shamoperated rats were prepared. They went through exactly the same procedure as described above with the exception that no blood was injected intracisternally. All surviving animals were neurologically examined using an established scoring system (Bederson et al., 1986, Menziers et al., 1992). After two days either autoradiographic measurements or harvesting of vessels were done (see below for details).

Example 2

Rat Subarachnoid Hemorrhage Model with Raf Inhibition

This group of animals went through the same procedure as the above-mentioned SAH animals. In addition they were treated with 20-50 µl; 10-6 M of SB386023-b (a kind gift from Dr A A Parsons, GSK, UK) or the same volume of vehicle repeatedly 6, 12, 24 and 36 h after the induced SAH. This dose was based on a previous in vivo study with SAH.

Rat Subarachnoid Haemorrhage Model with Protein Kinas C Inhibition

This group of animals went through the same procedure as the above-mentioned SAH animals. In addition, they were treated with the PKC inhibitor RO-31-7549 (Calbiochem, Sweden) or vehicle in conjunction with the operation and after the induced SAH. All animals treated with RO-31-7549 received five injections intracisternally of RO-31-7549 or vehicle in similar volume. Thus, 20 to 50 µl $10^{-6}$ mol/L of RO-31-7549 was injected intracisternally at 30 mins before the induced SAH and after the SAH 20 µl $10^{-6}$ mol/L of RO-31-7549 was administered repeatedly after 3, 6, 12, 24 and 32 h from the first RO-31-7549 injection. This dose was chosen on the basis of previous detailed work on isolated cerebral arteries (Hansen-Schwartz et al, 2002), the dose was chosen at near maximum inhibition and calculation of cerebrospinal fluid volume/turnover. RO-31-7549 is a selective PKC inhibitor with some isozyme specificity, primarily inhibiting classic PKCs (IC50 for PKCα=$10^{-7}$ mol/L, PKC$_{\beta I}$=$10^{-6.7}$ mol/L, PKC$_{\beta II}$=$10^{-6.8}$ v, PKCγ=$10^{-6.7}$ mol/L and PKCε=$10^{-6.8}$ mol/L) (Wilkinson et al, 1993).

Rat MCAO Model with MEk1/MEK2 Inhibitor

This group of animals went through the same procedure as the above-mentioned SAH animals. Two hours after the MCA occlusion, the rat was re-anesthetized to allow for withdrawal of the filament and subsequent reperfusion of the brain. In conjunction with the reperfusion (0 h), at 6 h or at 12 h afterwards, and at 24 h after the start of the reperfusion in the same animal, the rats were injected intraperitoneal with 30 mg/kg U0126 dissolved in dimethylsulfoxide (DMSO). In preliminary experiments we evaluated U0126 doses varying between 10 mg/kg and 100 mg/kg (n=3-6) (unpublished data); 30 mg/kg was the lowest that elicited a clear significant effect on infarct volume. Control rats were injected with an equal volume of DMSO at the same time points.

Example 3

Autoradiographic Measurements of Regional CBF

Regional and global cerebral blood flow was measured by a model originally described by Sakurada et al., (1978) and modified by Gjedde et al., (1980). In brief, after 48 hours of observation rats in the various groups (sham, SAH+vehicle and SAH treated with the raf inhibitor) were anaesthetized using 5% halothane in $N_2O/O_2$ (30:70). The animal was intubated and artificially ventilated with inhalation of 0.5-1.5% halothane in $N_2O/O_2$ (70:30) during the surgical procedure. The anaesthesia and the respiration were monitored by regularly withdrawing arterial blood samples for blood gas analysis (Radiometer AS, Denmark). A catheter to measure MABP was placed in the right femoral artery and a catheter for blood sampling was placed in the left femoral artery. This catheter was connected to a constant velocity withdrawal pump (Harvard apparatus 22, USA) for mechanical integration of tracer concentration. In addition, a catheter was inserted in one femoral vein for injection of heparin and for infusion of the radioactive tracer. The MABP was continuously monitored with a Powerlab Unit (ADInstruments, UK). A temperature probe was inserted into the rectum of the rat to record the temperature, which was regularly maintained at 37° C. The hematocrit was measured by a hematocrit centrifuge (Beckman Microfuge 11, USA). After 30 minutes of equilibration a bolus injection of 50 uCi of 14Ciodoantipyrine 4[N-methyl-14C] (Perkin-Elmer, Boston, USA) was given i.v. Arterial blood (122 µl) was withdrawn over 20 seconds. Immediately after this the animal was decapitated, the brain removed and immersed in isopentane (J. T. Baker, Deventer, Netherlands) chilled to −50° C. The arterial blood sample was transferred to liquid scintillation counting vials containing 1 ml mixture of Soluene-350 (Perkin-Elmer, Boston, USA) and Isopropanol (J. T. Baker, Deventer, Netherlands) (1:1). After 2 hours at 60° C., 0.2 ml of 30% hydrogen peroxide was added to the vials, and the samples were maintained at room temperature for 15-30 minutes. Thereafter the samples were kept at 60° C. for 30 minutes and 10-15 ml Hionic-Fluor (Perkin-Elmer, Foster, Calif., USA) was added. The β-radioactivity scintillation counting was performed on the samples with a program that included quench correction (Packard 2000 CA, Denmark). The 14C activity in the tissue was determined after sectioning the brain in 20 µm sections at −20° C. in a cryostat (Wild Leitz A/S, Glostrup, Denmark). The sections were exposed to x-ray films (Kodak, Denmark) together with 14C methylmethacrylate standards (Amersham Life Science, England) and exposed the films for 20 days. Densities of the autoradiograms were measured with a Macintosh computer equipped with an analog CF 4/1 camera (Kaiser, Germany) and a transparency flat viewer (Color-Control 5000, Weilheim, Germany). The 14C content was determined in several brain regions (see Table 2). The CBF was calculated from the brain tissue 14C4 activity determined by autoradiography using Gjedde et al.'s (1980) equation.

Example 4

Harvest of Cerebral Arteries

After 48 hours of observation sham, SAH treated with SB386023-b or treated with the PKC inhibitor RO-31-7549 or U0126 or SAH+vehicle operated rats (see above SAH model) were anaesthetized with $CO_2$ and decapitated. The brains were quickly removed and chilled in ice-cold bicarbonate buffer solution (see composition below). Under a dissection microscope, the middle cerebral artery (MCA), the basilar artery (BA) and circle of Willis were carefully dissected free from the brain and cleared of connective tissue. The MCA and BA were immediately mounted in myographs for in vitro pharmacology or snap frozen at $-80°$ C. and examined by real-time PCR.

In vitro Pharmacology Myograph Experiments For contractile experiments a sensitive myograph was used for recording the isometric tension in isolated cerebral arteries (Hogestatt et al., (1983, Mulvany and Helpern, 1977). The vessels were cut into 1 mm long cylindrical segments and mounted on two 40 μm in diameter stainless steel wires in a Myograph (Danish Myo Technology A/S, Denmark). One wire was connected to a force displacement transducer attached to an analog-digital converter unit (ADInstruments, Oxford, UK). The other wire was connected to a micrometer screw, allowing fine adjustments of vascular tone by varying the distance between the wires. Measurements were recorded on a computer by use of a PowerLab unit (ADInstruments). The segments were immersed in a temperature controlled buffer solution (37° C.) of the following composition (mM) NaCl 119, $NaHCO_3$ 15, KCl 4.6, $MgCl_2$ 1.2, $NaH_2PO_4$ 1.2, $CaCl_2$ 1.5 and glucose 5.5. The buffer was continuously aerated with oxygen enriched with 5% $CO_2$ resulting in a pH of 7.4. The vessels were stretched to an initial resting tone of 2 mN and then allowed to stabilize at this tone for 1 hour. The contractile capacity was determined by exposing the vessels to an isotonic solution containing 63.5 mM of K+, obtained by partial change of NaCl for KCl in the above buffer. The contraction induced by K+ was used as reference for the contractile capacity. Only vessels responding by contraction of at least 2.0 mN to potassium for BA and 0.8 mN to potassium for MCA were included in the study. The presence of the endothelium was checked by precontracting the vessel using 5-HT ($10^{-6.5}$M) (Sigma, St Louis, USA) and subsequently exposing the segments to carbachol ($10^{-5}$ M) (Sigma, St Louis, USA). A relaxant response of the precontracted tension was considered indicative of a functional endothelium (Hansen-Schwartz et al., 2003a).

Concentration-response curves were obtained by cumulative application of 5-CT (Sigma, St. Louis, USA) in the concentration range $10^{-12}$ to $10^{-5}$ M, ET-1 (AnaSpec, San Jose, USA) in the concentration range $10^{-14}$ to $10^{-7}$ M and Ang II (Sigma, St. Louis, USA) in the concentration range $10^{-12}$ to $10^{-6}$ M. Before application of Ang II the arteries were pretreated with the AT2 receptor antagonist PD123319 ($10^{-5.5}$ M) for 30 minutes (a kind gift from Dr P. Morsing, AstraZeneca, Molndal, Sweden).

Example 5

RNA Isolation

To quantify mRNA for the $ET_A$, $ET_B$ and 5-$HT_{1B}$ receptors, RT-PCR and real-time detection monitoring the PCR products was employed. Total cellular RNA was extracted from BA, MCA and circle of Willis using the Trizol RNA isolation kit (Invitrogen, USA) following the suppliers instructions. Briefly, the arteries were homogenized in 1 ml of Trizol (Invitrogen, Sweden) by using a TissueLyser (VWR, Sweden). Subsequently 200 μl of chloroform was added and the samples were incubated in room temperature for 3 min, followed by centrifugation at 15000 g for 15 min at 4° C. The supernatant was collected and the organic phase discarded. 200 μl of chloroform was again added to remove all traces of phenol and the samples were centrifuged at 15000 g for 15 at 4° C. The aqueous supernatant was again collected and to precipitate the RNA equal amount of isopropanol was added and the samples incubated overnight at $-20°$ C.

Subsequently, the RNA was centrifuged at 15000 g for 20 min at 4° C. The supernatant was discarded and the resulting pellet was washed with 75% ethanol, airdried and redissolved in diethylpyrocarbonate treated water. Total RNA was determined using a GeneQuant Pro spectrophotometer measuring absorbance at 260/280 (Amersham Pharmacia Biotech, Uppsala, Sweden).

Real-Time PCR

Reverse transcription of total RNA to cDNA was carried out using the Gene Amp RNA kit (Perkin-Elmer Applied Biosystems, USA) in a Perkin-Elmer 2400 PCR machine at 42° C. for 90 min and then 72° C. for 10 min. The real-time quantitative PCR was performed with the GeneAmp SYBR Green PCR kit (PE Applied Biosystems) in a Perkin-Elmer real-time PCR machine (GeneAmp 5700 sequence detection system). The above synthesized cDNA was used as a template in a 25 μl reaction volume and a no template was included in all experiments. The system automatically monitors the binding of a fluorescent dye to double-strand DNA by real-time detection of the fluorescence during each cycle of PCR amplification. Specific primers for the rat ETA, ETB and 5-HT1B receptor and house keeping gene elongation factor-1 (EF-1) were designed by using the Primer Express 2.0 software (PE Applied Biosystems) and synthesized by TAG Copenhagen A/S (Copenhagen, Denmark).

Receptor Primers Had the Following Sequences:

```
ET_A receptor forward:
5'-GTCGAGAGGTGGCAAAGACC-3' reverse:
5'-ACAGGGCGAAGATGACAACC-3'

ET_B receptor forward:
5'-GAT ACG ACA ACT TCC GCT CCA-3' reverse:
5'-GTC CAC GAT GAG GAC AAT GAG-3'

5-HT_1B receptor forward:
5'-TCC GGG TCT CCT GTG TAC GT-3' reverse:
5'-GGC GTC TGA GAC TCG CAC TT-3'
```

The housekeeping gene EF-1 is used as a reference, since it is continuously expressed to a constant amount in cells. The EF-1 primers were designed as follows:

EF-1 forward:
5'-GCA AGC CCA TGT GTG TTG AA-3'

EF-1 reverse:
5'-TGA TGA CAC CCA CAG CAA CTG-3'

The PCR reaction was carried out as follows: 50° C. for 2 min, 95° C. for 10 min and the following 40 PCR cycles with 95° C. for 15 sec and 60° C. for one min. Each sample was examined in duplicates. To verify that each primer-pair only generated one PCR product at the expected size a dissociation analysis was performed after each real-time PCR run. A blank control (without template) was used in all experiments. To prove that the cDNA of EF-1 and the ET and $5\text{-}HT_{1B}$ receptors were amplified with a similar efficacy during real-time PCR, a standard curve were made in which the CT values were plotted against cDNA concentration on the basis of the following equation: $CT=(\log(1+E))-1 \log (\text{concentration})$, where CT is the number of PCR cycles performed in one sample at a specific point of time, and E is the amplification efficiency with an optimal value of one. Standard curves for $ET_A$, $ET_B$, $5\text{-}HT_{1B}$ and EF-1 were performed by dilution of cDNA sample (1:10, 1:100 and 1:1000) (data not shown).

Example 6

Immunohistochemistry

The MCA and BA were dissected out and then placed onto Tissue TEK (Gibco) and frozen. They were then sectioned into 10 μm thick slices. The primary antibodies used were rabbit antihuman $ET_B$ (IBL, 16207), diluted 1:400, goat anti mouse $5\text{-}HT_{1B}$ (Santa Cruz Biotechnologies, sc-1461), diluted 1:100, $AT_1$ (Santa Cruz Biotechnologies), diluted 1:100, mouse anti rat CD31 (Serotec, MCA1746), diluted 1:200, and mouse anti rat smooth muscle actin (Serotec, MCA1905T) diluted 1:100. All dilutions were done in PBS with 10% fetal calf serum. The secondary antibodies used were donkeyantimouse Cy™5 conjugated (JacksonImmunoResearch, 715-175-150) 1:100, donkeyantirabbit Cy™3 conjugated (JacksonImmunoResearch, 711-165-152) 1:100 in PBS with 10% fetal calf serum. The antibodies were detected at the appropriate wavelength in a confocal microscopy (Zeiss, USA). As control, only secondary antibodies were used.

Calculations and Statistics

Data are expressed as mean±standard error of the mean (s.e.m.), and n refers to the number of rats. Statistical analyses were performed with Kruskal-Wallis non-parametric test with Dunn's post-hoc test, where $P<0.05$ was considered significant. In vitro Pharmacology Contractile responses in each segment are expressed as percentage of the 63.5 mM K+ induced contraction. Emax value represents the maximum contractile response elicited by an agonist and the pEC50 the negative logarithm of the drug concentration that elicited half the maximum response. For biphasic responses, Emax(1) and pEC50(1) describes the high affinity phase and Emax(2) and pEC50(2) describes the low affinity phase.

Real-Time PCR

PCR experiments were performed on BA, MCA and circle of Willis from SAH, SAH treated with raf inhibitor or PKC inhibitor and sham operated rats. Data were analysed with the comparative cycle threshold (CT) method (28). The CT values of EF-1 mRNA were used as a reference to quantify the relative amount of ETA, ETB and 5-HT1B mRNA. The relative amount of mRNA was calculated with the CT values of ETA, ETB and 5-HT1B receptor mRNA in relation to the CT values of EF-1 mRNA in the sample by the formula $X0/R0=2^{CtRCtX}$, where X0 is the original amount of target mRNA, R0 is the original amount of EF-1 mRNA, CtR is the CT value for EF-1 and CTX is the CT value for the target.

Immunohistochemistry

The images were analysed using the ImageJsoftware (http://rsb.info.nih.gov/ij/). The fluorescence in 4-6 different areas in each artery was measured and a mean value was calculated. These values are presented as percentage fluorescence in the SAH groups compared to the sham group, where the sham group is set to 100%.

Example 7

The Different Substances were Evaluate on Cortical Arteries

Cortical arteries and brain tissue samples were obtained from patients undergoing neurological surgery for brain tumors. The arteries obtained were carefully dissected free of connective tissue leaving the vessel with intact intima, media and adventitia. The vessels were cut into 1-mm long segments for in vitro pharmacological experiments and 3-mm for molecular biological analyses. The outer diameters were between 300 and 800 μm.

Organ Culture

The arterial segments were cultured for 48 hours at 37° C. in humidified 5% $CO_2$ and air in Dulbecco's modified Eagle's medium supplemented with pencillin (100 U/ml), streptomycin (100 μg/ml) and amphotericin B (25 μg/ml). The method of blood vessel culture has been described previously (Adner et al., 1996). The segments were cultured in the absence or presence of the MEK1/2 inhibitors U0126 (5 μM).

In Vitro Pharmacology Myograph Experiments

For contractile experiments a sensitive myograph was used for recording the isometric tension in isolated cerebral arteries (Hogestatt et al., 1983; Mulvany and Halpern, 1977). The vessels were cut into 1 mm long cylindrical segments and mounted on two 40 μm in diameter stainless steel wires in a Myograph (Danish Myo Technology A/S, Denmark). One wire was connected to a force displacement transducer attached to an analog-digital converter unit (ADInstruments, Oxford, UK). The other wire was connected to a micrometer screw, allowing fine adjustments of vascular tone by varying the distance between the wires. Measurements were recorded on a computer by use of a PowerLab unit (ADInstruments). The segments were immersed in a temperature controlled buffer solution (37° C.) of the following composition (mM) NaCl 119, $NaHCO_3$ 15, KCl 4.6, $MgCl_2$ 1.2, $NaH_2PO_4$ 1.2, $CaCl_2$ 1.5 and glucose 5.5. The buffer was continuously aerated with oxygen enriched with 5% $CO_2$ resulting in a pH of 7.4. The vessels were stretched to an initial resting tone of 2 mN and then allowed to stabilize at this tone for 1 hour. The contractile capacity was determined by exposing the vessels to an isotonic solution containing 63.5 mM of $K^+$, obtained by partial change of NaCl for KCl in the above buffer. The contraction induced by $K^+$ was used as reference for the contractile capacity (Hogestatt et al., 1983). Only vessels responding by contraction to potassium were included in the study. The same results were obtained for the different inhibitors used above which shows that all of them are candidates to be used to treat stroke.

Results

SAH Model

The total number of rats used in the study was 36; 12 in the sham group, 12 in the SAH+ vehicle group and 12 was used in the SAH+ treatment with SB386023-b group, 12 for the U0126 group, and 47 rats for the RO-31-7549 study. The mortality rate was 8% and there was no difference in the mortality rate between the groups. The rats did not show any distressed behaviour. They were moving around, eating, drinking and their fur was not sprawl. All surviving animals were neurologically examined using an established scoring system (21, 22). All SAH+ vehicle animals received a score of 1, and the sham and SB386023-b and RO-31-7549 treated groups got a score of 0. In all operated rats, mean arterial blood pressure (105±3 mmHg), partial pCO2 (38±3 mmHg), partial pO2 (108±4 mmHg), hematocrit (39±1 mmHg) values and temperature were within acceptable limits during the operation. No statistical difference was seen in physiological parameters between the groups; sham, SAH+ vehicle (henceforth only mentioned as SAH), SAH treated with SB386023-b, and SAH treated with U0126. As a result of injecting the blood the cortical blood flow dropped over both hemispheres to 10±5% of resting flow (there was no difference between the two Laser Doppler probe data) and the ICP increased from 9±2 to 126±9 mmHg. The Laser Doppler blood flow and the elevated ICP returned to the basal values within one hour of postoperative monitoring. There was no difference between the SAH groups.

The total number of rats used in the study was 47; 16 in the SAH groups, 15 in the sham group and 16 was used in the SAH+ treatment with RO-31-7549 group. The mortality rate of the animal model of SAH was 5% and there was no difference in the mortality rate between the groups. The rats did not show any distressed behaviour. They were moving around, eating, drinking and their fur was not sprawl.

All surviving animals were neurologically examined using an established scoring system (Bederson et al, 1986; Menzies et al, 1992). All SAH animals received a score of 1, and the sham and PKC treated groups got a score of 0. However, staining of coronal slices of the brain with 1% 2,3,5-triphenyltetrazolium chloride (TTC) did not show any changes to support the neurologic outcome. In all operated rats, MABP (101±3 mm Hg), partial $pCO_2$ (40±0.5 mm Hg), partial $pO_2$ (103±2 mm Hg), haematocrit (42±1 mm Hg) values and temperature were within acceptable limits during the operation. No statistical difference was seen in physiologic parameters between the groups; sham, SAH+ vehicle (henceforth only mentioned as SAH) and SAH treated with RO-31-7549. A result of injecting the blood the cortical blood flow dropped over both hemispheres to 20±3% of resting flow (there was no difference between the two Laser Doppler probe data) and the ICP increased from 10±1 to 129±10 mm Hg. The Laser Doppler blood flow and the elevated ICP returned to the basal values within 1 h of postoperative monitoring. There was no difference in the ICP and cortical blood flow between the two groups SAH and SAH treated with RO-31-7549 or vehicle. Injection of RO-31-7549 or vehicle alone had no effect on the cortical blood flow measured with Laser Doppler. The data for the raf group were similar.

Regional Cerebral Blood Flow (rCBF) to Evaluate the Overall Consequences of SAH

There was a significant global decrease in cerebral blood flow measured at 48 h in the SAH (n=5) group as compared to the control group (n=5) from 140±6 to 63±2 ml/100 g/min. Treatment with SB386023-b (n=6) (128±4 ml/100 g/min) 6 h after the SAH prevented the reduction in CBF seen after SAH. The SAH animals showed a reduction in the regional CBF in 15 of the 18 brain regions examined compared to the control operated rats. Treatment with SB386023-b at 6 h after SAH or treated with U0126 at 0 h or 6 h after the SAH prevented this reduction in rCBF and there was no difference as compared to the control group for any of the regions studied. The same degree of effect was seen when the blocker was given in conjunction with the SAH.

There was a significant global decrease in CBF in the SAH group (n=5) compared with the control group (n=5) from 60.10±3.53 to 131.30±7.04 ml/100 g/min, respectively (P<0.05). Treatment with RO-31-7549 (n=5) prevented the marked reduction in CBF seen after SAH (FIG. 3). The SAH animals showed a reduction in the rCBF in 14 of the 18 brain regions examined compared with the control operated rats. Treatment with RO-31-7549 prevented this reduction in rCBF, and there was no difference as compared with the control group for any of the regions studied.

Functional In Vitro Pharmacology

K+-induced contractions did not differ significantly between the cerebral arteries from the different groups. Emax and pEC50 values for respective group are presented in Table 3.

Contractile Response to ET-1

In the MCA and BA from SAH rats (n=6) ET-1 showed a leftward shift of the concentrationresponse curve which indicates an enhanced contractile response to ET-1 as compared to the sham-operated rats (n=6) where a sigmoidal curve was obtained. Treatment with SB386023-b (n=6) produced a significantly attenuated ET-1 induced response, compared to the rats with induced SAH. Interestingly there was no significant difference in the contractile response between sham and SB386023-b treated rats. Similar data were seen with U0126 treatment.

In the MCA and BA from SAH rats (n=5) ET-1 showed a leftward shift of the curve, which indicates an enhanced contractile response to ET-1as compared with the sham-operated rats (n=4 to 5) where a normal sigmoidal curve was obtained. Treatment with RO-31-7549 (n=7 to 8) produced a significantly attenuated ET-1 induced response, compared with the rats with induced SAH (P<0.05). Interestingly, there was no significant difference in the contractile response between sham and RO-31-7549 treated rats. In the present study, application of the specific ETB receptor agonist S6c alone did not give rise to any contraction in rats with induced SAH, in rats with induced SAH and treated with PKC inhibition, or in sham operated rats in the MCA or the BA (data not shown). Desensitization of the ETB receptor with S6c induced an attenuated contractile response to ET-1 in the rats with induced SAH (data not shown). This implicates that the enhanced contractile effect after SAH is ETB dependent. This is in support of studies previously published with selective endothelin receptor antagonists (Hansen-Schwartz and Edvinsson 2000; Hansen-Schwartz et al, 2003b).

Contractile Response to 5-CT

5-CT gave rise to a biphasic concentrationdependent contraction, indicating the presence of the two 5-HT receptor subtypes 5-HT1B and 5-HT2A as verified by previous detailed antagonist studies (29). In both MCA and BA from rats with induced SAH (n=4-5) 5-CT gave rise to an elevated Emax(1), Emax(2) and pEC50(2) as compared to the sham-operated rats (n=4-5) (p<0.05, FIG. 4; Table 3). In BA treatment in vivo with SB386023-b (n=6) downregulated, both the first 5-HT1B and the second 5-HT2A phases as compared to the rats with induced SAH (FIG. 4). In the MCA treatment with SB386023-b (n=6) (or U0126) significantly reduced the Emax(1) (p<0.05) and tended to decrease the Emax(2), pEC50(1) and pEC50(2) compared to the SAH induced rats. Similar data on SB386023 were seen when the raf blocker were given acutely at the SAH induction.

5-CT gave rise to a biphasic concentration-dependent contraction, indicating the presence of two receptors $5-HT1_B$ and 5-HT$_{2A}$ as verified by previous detailed antagonist studies (Hoel et al, 2001). In both MCA and BA from rats with induced SAH (n=4 to 5) 5-CT gave rise to an elevated Emax (1), Emax(2) and pEC50(2) as compared with the sham-operated rats (n=4 to 5) (P<0.05, FIG. 5; Table 4). In BA treatment in vivo with RO-31-7549 (n=6) downregulated, both the first 5-HT1B and the second 5-HT2A phases as compared with the rats with induced SAH (FIG. 4C). In the MCA treatment with RO-31-7549 (n=6) significantly reduced the Emax(1) (P<0.05) and had a tendency to decrease the Emax(2), pEC50(1) and pEC50(2) compared with the SAH induced rats (FIG. 5, Table 4).

Contractile Response to Ang II

In MCA from rats with induced SAH (n=6) Ang II (via AT1) induced a concentration-dependent contraction (in the presence of the AT2 receptor antagonist PD123319). Treatment with SB386023-b (n=6) produced a significantly attenuated Ang II induced response, compared to the rats with induced SAH. Interestingly there was no significant difference in the contractile response between sham (n=5) and SB386023-b treated rats (FIG. 4; Table 5). Ang II did not induce an increased contractility in the BA after SAH.

Figure 1B:
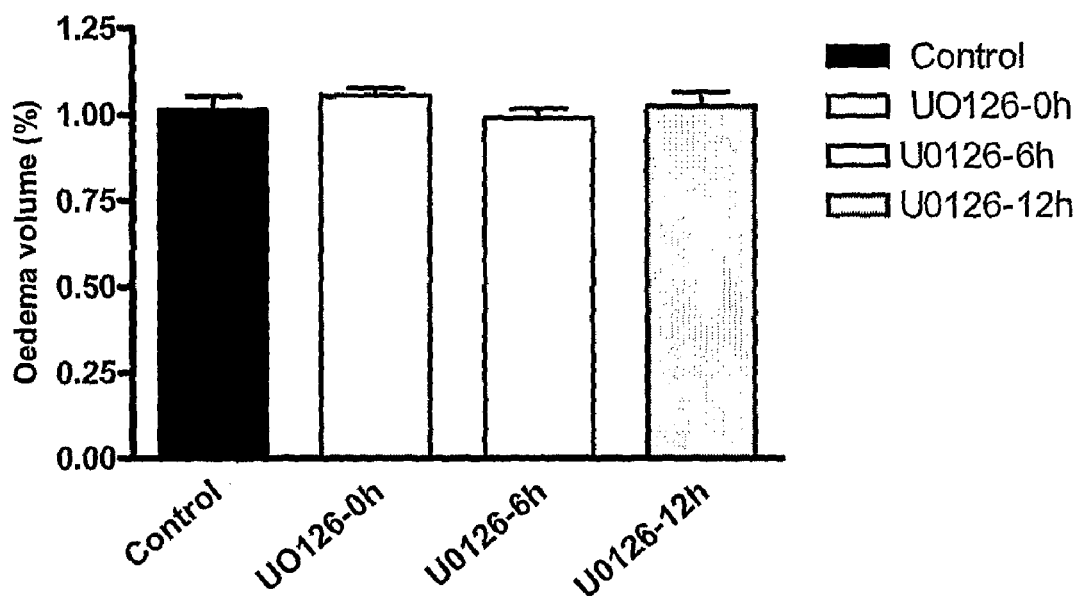

The results are summarised in FIG. 1. Same results were obtained by the other inhibitors.

FIG. 1A:

Analysis of the brain damage (% of total volume) showing a significantly decreased the size of the ischemic area in animals treated with U0126 starting at 0h (11.8±2%**) and 6 h (14.6±3%*) after MCAO as compared to the control group (24.8±2%) and treated after 12 h (20.3±1%), *P<0.05**P<0.01.

FIG. 1B:

Analysis of the oedema (% of total volume) showing no significant change in the U0126 treated groups (0h; 1.05±0.02, 6 h; 0.98±0.02 and 12 h; 1.02±0.04) with the control rats (1.01±0.03). Values are the mean±s. e. m. and n=6-7.

Quantitative mRNA Expression

The standard curves for each primer pair had almost similar slopes, demonstrating that EF-1, ETA, ETB, 5-HT1B, AT1 and AT2 cDNA were amplified with the same efficiency (data not shown). In each PCR experiment, a no template control was included, and there were no signs of contaminating nucleic acids in the samples. Since the results from the different brain arteries examined MCA, BA and circle of Willis (n=7-10) were identical, they were grouped together in the statistical analysis. The results showed that treatment with SB386023-b inhibited the enhanced expression of ETB, 5-HT1B and AT1 receptor mRNA levels significantly as compared to control. There was no difference in the expression of ETA and AT2 receptor mRNA levels between the three groups sham, SAH and SAH treated with SB386023-b (data not shown). Similar inhibition data were seen both when SB 38023b, U0126 or the PKC inhibitor RO-31-7548 were given in conjunction with the ischemia.

Protein Expression Examined with Immunohistochemistry

Selective antibodies towards the phosphorylated ERK, ET$_B$, 5-HT$_{1B}$ and AT$_1$ receptors visualized their smooth muscle cell localization using confocal microscopy. Double immunohistochemistry staining versus smooth muscle actin, expressed in the smooth muscle cells, and CD31, expressed in the endothelial cells, were performed to verify the localization. The ET$_B$ receptor protein was expressed on the smooth muscle cells and this signal was increased in SAH (167±4%) as compared to sham (100±3%). Similarly the 5-HT$_{1B}$ (180±2%) and AT$_1$ (168±7%) receptor proteins were expressed more in SAH as compared to sham (100±7%) and (100±7%); respectively (p<0.05 for all). Treatment with the ERK1/2 inhibitor SB386023-b prevented the upregulation of ET$_B$ (109±5%), 5-HT$_{1B}$ (121 15±23%) and AT$_1$ (105±10%) receptor protein levels in the smooth muscle cell layer as compared to the SAH (FIG. 6). After SAH the pERK1/2 level (188±7%) was increased in the smooth muscle cells as compared to sham (100±3%). Treatment with the raf inhibitor prevented the pERK (102±5%) activation.

The invention claimed is:

1. A method of treating a patient for ischemic damage, comprising:
   administering a medicament comprising at least one inhibitor selected from the group consisting of U0126, SB590885, and SB386023b to the patient to reduce the ischemic damage, wherein said medicament is administered to the patient from greater than 1 hour up to 12 hours after onset of the ischemic damage.

2. A method according to claim 1, wherein said inhibitor is U0126.

3. A method according to claim 1, wherein said inhibitor is SB590885 or SB386023b.

4. A method according to claim 1, wherein said medicament further comprises a pharmaceutically acceptable diluent, excipient, buffer, or carrier.

5. A method according to claim 1, wherein said medicament is administered to the patient intravenously, intrathecally, or intraventricularly.

6. A method according to claim 1, wherein said medicament is administered to the patient intraventricularly.

7. A method according to claim 1, wherein the patient is a mammal.

8. A method according to claim 1, wherein said medicament is administered to the patient from greater than 1 hour up to 6 hours after onset of the ischemic damage.

9. A method according to claim 1, wherein the ischemic damage is associated with cerebral ischemia or subarachnoid haemorrhage.

10. A method according to claim 1, wherein the ischemic damage is associated with an ischemic brain injury.

11. A method according to claim 10, wherein the ischemic brain injury is a stroke.

* * * * *